(12) United States Patent
Bougherara

(10) Patent No.: US 8,124,675 B2
(45) Date of Patent: Feb. 28, 2012

(54) ADHESIVE COMPOSITION

(75) Inventor: Chaabane Bougherara, Frederiksberg (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 12/923,943

(22) Filed: Oct. 15, 2010

(65) Prior Publication Data

US 2011/0034847 A1    Feb. 10, 2011

Related U.S. Application Data

(63) Continuation of application No. 10/570,258, filed on Mar. 2, 2006, now Pat. No. 7,842,752.

(30) Foreign Application Priority Data

Sep. 2, 2003 (DK) ................................ 2003 01258
Dec. 17, 2003 (DK) ............................... 2003 01871

(51) Int. Cl.
*C08L 83/04* (2006.01)

(52) U.S. Cl. ........................................ 524/28; 524/588

(58) Field of Classification Search .................. 524/28, 524/588; 525/477

See application file for complete search history.

(56) References Cited

U.S. PATENT DOCUMENTS 4,898,920 A * 2/1990 Lee et al. ...................... 525/477

OTHER PUBLICATIONS

Snejdrova et al. (Abstract of "Effect of sodium chloride on elasticity of silicone matrices", Ceska Slov Farm., Sep. 2002; 51(5): 248-51).*

* cited by examiner

*Primary Examiner* — Ling Choi
*Assistant Examiner* — Chun-Cheng Wang
(74) *Attorney, Agent, or Firm* — Jacobson Holman PLLC

(57) ABSTRACT

The invention relates to an adhesive composition comprising hydrophilic silicone elastomers and hydrophobic silicone elastomers and optionally water absorbent material, wherein the ratio between the hydrophilic silicone elastomers and the hydrophobic silicone elastomers is from 95:5 to 5:95. The adhesive is suited for medical use due to its skin-friendliness. The invention further relates to a medical device comprising said adhesive composition.

37 Claims, No Drawings

ADHESIVE COMPOSITION

This is a nationalization of PCT/DK2004/000584 filed 2 Sep. 2004 and published in English.

CROSS-REFERENCE TO RELATED APPLICATION

This is a continuation application of U.S. patent application Ser. No. 10/570,258, filed Mar. 2, 2006 now U.S. Pat. No. 7,842,752, and hereby incorporated in its entirety by reference.

BACKGROUND OF THE INVENTION

1. Field of the Invention The invention relates to an adhesive composition and a medical device comprising an adhesive composition.

2. Description of the Related Art

Medical devices, such as wound care devices and ostomy appliances may comprise adhesives for direct contact with the skin. It is important that the adhesive is skin-friendly, as the skin often is damaged or just extremely fragile, especially when handling chronic wounds. Different suitable adhesives are known in the art. Hydrocolloid adhesives are often used, due to their permeability and good absorption properties. Acrylic adhesives may also be used, especially for thin applications, as the permeability is low.

Silicone adhesives are very skin-friendly and very suitable for donating active agents, such as in medicated patches, but they are also rather occlusive and hydrophobic, which is a mayor disadvantage for a product being worn for prolonged period, such as wound dressings, ostomy appliances or incontinence devices.

Attempts have been made for preparing a more hydrophilic silicone adhesive. However, these adhesives tend to be difficult to remove due to a higher tack and lower cohesion, and are thus not very useful for application to fragile or damaged skin.

Another drawback connected to the use of silicone adhesives is the poor absorption properties. This problem may be solved by incorporating absorbent material e.g. in the form of super absorbent particles.

International patent application No. WO 02/087642 discloses an adhesive comprising a hydrophilic phase and a hydrophobic phase. The hydrophobic phase may be a silicone elastomer and the hydrophilic phase may be a water absorbing mixture of hydrophilic polymers of non-silicone origin.

In International patent application No. WO 02/076519 is disclosed a silicone-based moisture absorbing matrix for wound care products. The sticky matrix comprises silicone, gelling agent and optionally a silicone resin. Both silicone compounds are hydrophobic and the reference is silent with respect to the use of hydrophilic silicone.

SUMMARY OF THE INVENTION

The object of the present invention is to provide an adhesive composition, being skin-friendly and at the same time having good permeability properties.

Another object of the invention is to provide a silicone adhesive with absorption properties.

Yet another object of the invention is to provide a skin-friendly adhesive with a good cohesion to the skin and yet easy to remove.

Still another object of the invention is to provide a skin-friendly adhesive that reduces cell-stripping when removed from the skin.

Still another object of the invention is to provide an adhesive with good cohesion.

DETAILED DESCRIPTION OF THE PRESENT INVENTION

The invention relates to an adhesive composition comprising hydrophilic silicone elastomers and hydrophobic silicone elastomers and optionally water absorbent material, wherein the ratio between the hydrophilic silicone elastomers and the hydrophobic silicone elastomers is from 5:95 to 95:5.

The ratio between the hydrophilic silicone elastomers and the hydrophobic silicone elastomers may be from 10:90 to 90:10, preferably 20:80 to 80:20, more preferred 30:70 to 70:30 and most preferred 40:60 to 60:40.

Preferably, the ratio between the hydrophilic silicone and the hydrophobic silicone is from 10:90 to 40:60, more preferably from 20:80 to 30:70.

In one embodiment of the invention the ratio between the hydrophilic silicone and the hydrophobic silicone is from 5:95 to 50:50. In another embodiment of the invention ratio between the hydrophilic silicone and the hydrophobic silicone is from 95:5 to 50:50.

The ratio may in one embodiment of the invention be 25:75.

In another embodiment of the invention, the ratio between the hydrophilic silicone and the hydrophobic silicone is from 90:10 to 60:40, more preferably from 80:20 to 70:30.

In a preferred embodiment of the invention the ratio is 75:25.

By mixing hydrophobic silicone and hydrophilic silicone into an adhesive composition the interaction between the two groups of polymers are optimal, due to their related nature, compared to mixtures of hydrophobic silicone and other hydrophilic polymers than silicones.

Silicones such as trimethylsilyloxane terminated polydimetylsiloxane, are hydrophobic. These have an advantage of being inert to hydrophilic substances, which means that these substances are not dissolved in silicone and therefore are able to migrate out of the silicone. This explains why silicone is a good as drug release matrix.

For the purpose of this invention we need a silicone that is relatively less hydrophobic than trimethylsilyloxy-terminated polydimetylsiloxane but still can be used as a PSA (pressure sensitive adhesive) adhesive.

Hydrophobic silicones can be made hydrophilic by replacing some of the methyl groups along the chain or the chain ends with hydrophilic moieties well-known to those skilled in the art, such moieties may be oxymethylene and/or oxypropylene, acrylate amide, amines imines etc. The hydrophilicity or hydrophobicity may also be adjusted to the desired value by radio frequency or electrical current phase plasma treatment or corona treatment of the silicone fluid stream that passes into a chamber where plasma or corona is generated, and that or these monomer moieties that renders hydrophobic silicone hydrophilic is/are introduced.

Hydrophilic silicones capable of absorbing small amounts of water are known. An example may be Silicone 4000 series produced by DOW Corning. The water absorption may be further increased by incorporating water-absorbing material such as CMC or cross-linked acrylates. However, such silicone adhesive has low cohesiveness and is thus unsuitable in use for medical devices.

It has surprisingly been shown that the cohesiveness of the silicone adhesive may be increased by combining hydrophobic and hydrophilic silicone.

As a measure of the right combination of the amount of hydrophobic and hydrophilic silicone providing an adhesive composition with an optimal total hydrophilicity the surface energy can be used. The surface energy of the composition according to the present invention, measured in terms of water-in-air contact angle for a fully cured silicone mixture against a glass plate, without the absorbing agent and other ingredients mentioned in examples below, is preferably between 65 and 105 degree, more preferred between 75 and 100 degree and most preferred between 80 and 95 degree.

The surface energy can be measured by the water-in-air contact angle method known in the art, where the angle between a drop of distilled water and the surface of the substrate is measured.

To supplement contact angle findings, surface energy is also determined from the chemical structure of the silicone mixtures using the surface and interfacial tension of polymers, oligomers, plasticizers, and additives involved in the composition. These data are available in polymer handbooks.

The cohesiveness of the adhesive of the present invention is important when the adhesive has to be removed from a skin or wound site. Low cohesiveness may result in adhesive residues left on the skin or wound site or in the areas surrounding the wound site, and/or trauma while removing the adhesive due to a high peel force.

The ratio that suits both water absorption and gel cohesiveness may also influence the peel force of the PSA to be achieved.

The actual peel span of silicone elastomers lies between over 70 N for a 100% hydrophilic elastomer to around 0.5 N for 100% hydrophobic elastomer.

The peel force of the adhesive of the present invention may be from 1 N to 20 N measured according to 180 degree method DS/EN/28510-2.

In order for an adhesive composition to be suitable for medical use it is preferred that the peel force between 1 N and 10 N, more preferably the peel force is from 1 N to 5 N.

Peel force and gel cohesiveness can be influenced by varying the ratio between the hydrophilic and the hydrophobic silicone. Furthermore, the peel force may be further adjusted by incorporating some other ingredients such as kaolin, crystalline silica magnesium oxide, calcium carbonate or other reinforcing fillers, plasticisers, such as a low molecular silicone oil, e.g. hexamethylene disiloxane, soya bean oil or the derivative thereof, castor oil or the derivative thereof, or other additives known to persons skilled in the art.

Examples of additives may be UV stabilizers such as those known under trade name "Irganox, Cyanox, Hostanox", antioxidants, and cross-linking agents such as peroxides, divinylbenzene. Other suitable compounds may be acrylic or vinyl ended silicone moieties having an average molecular weight ranging 100 to 10.000. These moieties are also referred to as cross-linking agents. Adhesion promoters may also be added to the silicone mixtures in order to improve the affinity of the silicone adhesive for the substrate onto which the adhesive is to be applied. The adhesion promoters may be silicone based, such as those commercialized by Dow Corning under the name "Silane Z-603". Titan based such those commercialized by Du Pont under the name "Tyzor AA 105" may also be used. Adhesion promoters can be mixed into the silicone composition prior to coating and curing, or simply used as a primer onto the substrate carrier prior to coating.

Silicone adhesives are typically composed of two main components, a siloxane polymer and a silicate resin. Silicone adhesives are either supplied pre-cross linked, supplied in a hydrocarbon solvent or in a silane solvent. Or as a two-part system where the first part comprises a cross-linking agent and the other part comprises a catalyst that in most cases is an organometallic catalyst, typically an organoplatinum catalyst.

Examples of suitable silicones for the present invention may be polydimethylsiloxane, polymetylphenylsiloxane, alkylsiloxane, alkyoxysiloxane. An example of a suitable silicate resin may be trimetylsiloxy silicate, also known as tetrakis silicate.

Preferred silicones may be polyorganesiloxane such as polydimethylsiloxane, poly(oxymethylsilylene), poly(oxyethylsilylene) or mixtures thereof, and/or silicones corresponding to general formula shown below:

R—[Si(2R)—O—Si(2R)—] where R can generally be a methyl and/or ethyl group or can be substituted by one or several of the following groups —NH2, epoxy, acrylate, metacrylate, acrylamide, ethylene glycol, propylene glycol, halide (Cl, Br, F), maleic anhydride. The degree of substitution can vary from 0 to 90% preferably from 5 to 50% and more preferably from 5 to 20%.

The hydrophilic and the hydrophobic silicone may be based on the same silicone elastomer, or they may be based on different silicone elastomers. By using the same type of elastomers the mixing of the two elastomers may be facilitated.

In one embodiment of the invention the hydrophilic silicones may be silicones sold by Dow Corning under the name BIO-PSA, the series 7-4000 are most preferred. Other silicones such as those known as RTV (room temperature vulcanisable) may also be used when rendered less hydrophobic using the grafting techniques known in the art.

The hydrophobic silicone may preferably be RN silicones, such as those sold by Dow Corning, in a preferred embodiment of the invention the series 7-9000. Other silicones may be suitable.

The molecular weight of the silicone elastomers should be in the range of 50,000 to 1,000,000, preferably from 100,000 to 500,000, and more preferably from 50,000 to 250,000. The molecular weight of the hydrophobic and the hydrophilic elastomers may be essentially the same.

In one embodiment the molecular weight of the hydrophilic silicone elastomer is considerably smaller than the molecular weight of the hydrophobic silicone elastomer.

In a further embodiment of the invention the adhesive may be in the form of a foam.

The foam may be obtained by promptly releasing the pressure of pressurized cured silicone adhesive while it is still hot. Pressurization and nitrogen, and carbon dioxide may also be used to control the structure of the foam. Other blowing agents well known in the art may also be used in order to control the foaming time as well as the foam structure. By foaming the adhesive of the present invention a silicone adhesive with a better MVTR (moisture and vapor transmission rate) is achieved, and furthermore, the adhesive obtains cushioning effect too. These two characteristics may also be obtained by mixing water-soluble particles into the silicone composition, after curing of the adhesive; these particles are leached in the water, leaving small craters, through which a better MVTR may be obtained. Another way of increasing the MVTR is mixing a fluid into the silicone composition; the fluid has a low boiling point and is not immiscible with silicone. After coating and curing, the immiscible fluid lies within the coating as a micro droplets. The micro droplets of low boiling points fluid are evacuated by vacuum. The resulting adhesive will be in the form of a microporous mass with improved MVTR.

The composition of the present invention may optionally comprise water absorbent material. The incorporation of absorbent material may increase the absorbency and the MVTR of the adhesive.

The initial absorbency of the adhesive of the present invention may be increased by the addition of water absorbent material.

The water absorbent material may be in the form of particles or fibers.

The water absorbent material is preferably selected from the group of carboxy methyl cellulose (CMC) such as those sold by Hercules under the trade name Aquasorb® or crosslinked polyoxyethelenes, polyoxypropylenes, polyoxy (ethylene-propylene), such as those commercialized by Veramatrix A/S, under the generic name Versabeads®, or crosslinked polyacrylates, known as super absorbing particles (SAP), such as those sold by Atofina under the trade name Norsocryl®, acrylates, alginates, chitosans, polysaccharides and derivatives or mixtures thereof.

The adhesive of the present invention is especially suitable for adhering to the skin or mucous of a living being, such as a human. The adhesive is skin-friendly, provides a good tack, high flexibility, softness, permeability and is easy to remove. The adhesive may be suitable as a medical adhesive in medical devices, such as wound dressings, ostomy appliances, incontinence devices and other situations where a highly skin-friendly adhesive is desired.

The invention further relates to a wound care device comprising an adhesive composition comprising hydrophilic silicone elastomers and hydrophobic silicone elastomers and optionally water absorbent material, wherein the ratio between the hydrophilic silicone elastomers and the hydrophobic silicone elastomers is from 5:95 to 95:5.

Still further, the invention relates to an ostomy device comprising an adhesive composition comprising hydrophilic silicone elastomers and hydrophobic silicone elastomers and optionally water absorbent material, wherein the ratio between the hydrophilic silicone elastomers and the hydrophobic silicone elastomers is from 5:95 to 95:5.

Materials And Methods

Hydrophilic silicone resin from Dow Corning sold under the trade name BIO-PSA 7-4300.
Hydrophobic silicone resin from Dow Corning sold under the trade name silicone 7-9800. Silicone 7-9800 is a two parts system with a component A comprising a catalyst and a component B comprising a cross-linking agent.
CMC
Acrylate polymer from Atofina sold under the trade name Norsocryl XFS.
Versa-beads-O from Versamatrix
Versa-beads-A from Versamatrix
Versa-beads-E from Versamatrix
N-hexane
Hexamethyldisiloxane Example 1

Preparation of Adhesive 100 parts of BIO-PSA 7-4300 were dissolved in 40 parts of n-hexane under stirring at room temperature for 20 minutes. 50 parts of silicone 7-9800 (component A and B in a one to one ratio) were added and the mixture was stirred for another 5 minutes, 20 parts of CMC were then added. The mixture was stirred for 3 minutes. From the mixture a 500 microns film was coated on a polyurethane film having 350 microns in thickness. After the n-hexane has evaporated, strips of 10 cm in length and 2 cm in width were cut and peel force test at 180 deg. was performed and an average peel force of 2.5 N was measured. Test of water uptake was also performed and an absorption of 800 gsm. (gram per square meter) after 24 hours was determined.

The adhesive was applied on to human skin and showed no cell stripping after removal, compared to a conventional adhesive.

Example 2

An Ostomy Device

Same as Example 1, except that CMC was replaced by 20 parts of Norsocryl XFS. n-hexane was replaced by 40 parts of HMDS (hexamethylene disiloxane). A peel force of 1.8 N was determined according to the method described in Example 1, and a water uptake of 3400 gsm. after 24 hours was measured. The adhesive was used for attaching an ostomy device directly to the skin. After removing of the device no traces of skin irritation or cell stripping was noticed.

Example 3

An Urine Collecting Device

Same as Example 1 except that more Pt based catalyst was added, by using silicone 7-9800 where component A and B were in a ratio 60:40 . . . 7.6 N in peel force were obtained when the composition was cured for at least 24 hours at 40° C., and 7 N when the composition was cured for at least 24 hours at 80° C. The adhesive was used for attaching a urine collector to male genital organ, the adhesive provided a tight and leakage proof fit and the patient suffered no pain while removing the device.

Example 4

Hydrophilic Silicone Adhesive With CMC 100 parts of BIO-PSA 7-4300 was dissolved in 40 parts of n-hexane under stirring at room temperature for 20 minutes. 20 parts of CMC were then added. The mixture was stirred for 3 minutes. From the mixture a 500 microns film was coated on a polyurethane film having 35 microns in thickness. After the n-hexane had evaporated, strips of 10 cm in length and 2 cm in width were cut and peel force was determined at 180 deg. A peel force of 14.8 N was obtained. Water uptake was also measured by immersion in water and an absorption of 1162 gsm per 24 hours (gram per square meter) was found. After 24 hours the adhesive began to decompose due to the lack of cohesiveness of the adhesive.

Example 5

Hydrophilic/Hydrophobic Silicone With CMC 70 parts of BIO-PSA 7-4300 was dissolved in 40 parts of n-hexane under stirring at room temperature for 20 minutes, and mixed with 30 parts of silicone 7-9800. 20 parts of CMC were then added. The mixture was stirred for 3 minutes. From the mixture a 500 microns film was coated on a polyurethane film having 35 microns in thickness. After the n-hexane had evaporated, strips of 10 cm in length and 2 cm in width were cut and peel force was determined at 180 deg. A peel force of 12.0 N was obtained. Water uptake was also measured by immersion in water and an absorption of 1062 gsm per 24 hours (gram per square meter) was found. After 24 hours the adhesive was still cohesive and did not dissolve or disintegrate in the water.

Example 6

Adhesive With Improved MVTR Prepared By Use of NaCl 90 parts of silicone 7-9800 were mixed with 5 parts of silicone 7-4300 dissolved in n-hexane, then 25 part of CMC were added and the mixture was stirred for 3 minutes. The mixture was then coated on a PU film, small beads of 1 mm in diameter of NaCl were spread on the surface of the coating (NaCl beads covered 25% of the total area), When the coating was cured the film was immersed in water for three hours, thus dissolving the beads. The MVTR was increased from 900 gr/m$^2$/24 h (without NaCl treatment) to 1200 gr/m$^2$/24 h (after NaCl treatment).

Example 7

Adhesive With Improved MVTR Prepared By Use of Blowing Agent 90 parts of silicone 7-9800 were mixed with 10 parts of silicone 7-4300 dissolved in n-hexane, 25 part of CMC were added and stirred for 3 minutes. The mixture was coated on a PU film, small beads of 1 mm in diameter made of a mixture of citric acid and backing soda were spread on the surface of the coating (the beads covered 25% of the total area. When the coating was cured the film was immersed in water for 30 min, and the beads were dissolved. The MVTR was increased from 900 gr/m2/24 h to 1500 gr/m$^2$/24 h.

Example 8

Adhesive With Improved MVTR Prepared By Using PEG 95 parts of silicone 7-9800 and 5 parts of silicone 7-4300 dissolved in n-hexane were mixed with 25 part of CMC, and 25 parts of polyethylene glycol 600 were added and gently stirred to favor the formation of microdroplets, after 3 minutes of stirring. The mixture was coated on a PU film, and cured. When the coating was cured the film was exposed to vacuum for 30 min. The MVTR was increased from 900 gr/m2/24 h to 1100 gr/m$^2$/24 h.

The invention claimed is:

1. An adhesive composition comprising a hydrophilic silicone elastomer and a hydrophobic silicone elastomer in a ratio (w/w) from 5:95 to 95:5, and sodium chloride.

2. The adhesive composition of claim 1, further containing a water absorbent material.

3. The adhesive composition of claim 2, wherein the water absorbent material is either in the form of particles or fibers.

4. The adhesive composition of claim 3, wherein the water absorbent material is selected from the group consisting of carboxymethyl cellulose, acrylates, alginates, chitosans, polysaccharides and derivatives and mixtures thereof.

5. An adhesive composition according to claim 1, wherein a mixture of the silicone components has a water-in-air contact angle between 65 and 105 degrees.

6. An adhesive composition according to claim 1, wherein the adhesive composition has a peel force from 1 to 20 N.

7. An adhesive composition according to claim 1, wherein the hydrophilic silicone elastomer is a polyorganosiloxane elastomer.

8. An adhesive composition according to claim 1, wherein the hydrophobic silicone elastomer is a polyorganosiloxane elastomer.

9. An adhesive composition according to claim 1, wherein the hydrophilic silicone elastomer and the hydrophobic silicone elastomer are based on the same silicone elastomer.

10. An adhesive composition according to claim 1, wherein the molecular weight of each of the hydrophilic silicone elastomer and the hydrophobic silicone elastomer is between 50,000 and 1,000,000.

11. A wound care device comprising a substrate and an adhesive composition, the adhesive composition containing a hydrophilic silicone elastomer and a hydrophobic silicone elastomer in a ratio (w/w) from 5:95 to 95:5, and sodium chloride.

12. The wound care device according to claim 11, wherein the adhesive composition further contains a water absorbent material.

13. The wound care device according to claim 12, wherein the water absorbent material is either in the form of particles or fibers.

14. The wound care device according to claim 13, wherein the water absorbent material is selected from the group consisting of carboxymethyl cellulose, acrylates, alginates, chitosans, polysaccharides and derivatives and mixtures thereof.

15. The wound care device according to claim 11, wherein a mixture of the silicone components has a water-in-air contact angle between 65 and 105 degrees.

16. The wound care device according to claim 11, wherein the adhesive composition has a peel force from 1 to 20 N.

17. The wound care device according to claim 11, wherein the hydrophilic silicone elastomer is a polyorganosiloxane elastomer.

18. The wound care device according to claim 11, wherein the hydrophobic silicone elastomer is a polyorganosiloxane elastomer.

19. The wound care device according to claim 11, wherein the hydrophilic silicone elastomer and the hydrophobic silicone elastomer are based on the same silicone elastomer.

20. An ostomy device comprising a substrate and an adhesive composition, the adhesive composition containing a hydrophilic silicone elastomer and a hydrophobic silicone elastomer in a ratio (w/w) from 5:95 to 95:5, and sodium chloride.

21. The ostomy device according to claim 20, wherein the adhesive composition further contains a water absorbent material.

22. The ostomy device according to claim 21, wherein the water absorbent material is either in the form of particles or fibers.

23. The ostomy device according to claim 22, wherein the water absorbent material is selected from the group consisting of carboxymethyl cellulose, acrylates, alginates, chitosans, polysaccharides and derivatives and mixtures thereof.

24. The ostomy device according to claim 20, wherein a mixture of the silicone components has a water-in-air contact angle between 65 and 105 degrees.

25. The ostomy device according to claim 20, wherein the adhesive composition has a peel force from 1 to 20N.

26. The ostomy device according to claim 20, wherein the hydrophilic silicone elastomer is a polyorganosiloxane elastomer.

27. The ostomy device according to claim 20, wherein the hydrophobic silicone elastomer is a polyorganosiloxane elastomer.

28. The ostomy device according to claim 20, wherein the hydrophilic silicone elastomer and the hydrophobic silicone elastomer are based on the same silicone elastomer.

29. A urine collector for a male genital organ comprising a substrate and an adhesive composition, the adhesive composition containing a hydrophilic silicone elastomer and a hydrophobic silicone elastomer in a ratio (w/w) from 5:95 to 95:5, and sodium chloride.

30. The urine collector according to claim 29, wherein the adhesive composition further contains a water absorbent material.

31. The urine collector device according to claim 30, wherein the water absorbent material is either in the form of particles or fibers.

32. The urine collector according to claim 31, wherein the water absorbent material is selected from the group consisting of carboxymethyl cellulose, acrylates, alginates, chitosans, polysaccharides and derivatives and mixtures thereof.

33. The urine collector according to claim 29, wherein a mixture of the silicone components has a water-in-air contact angle between 65 and 105 degrees.

34. The urine collector according to claim 29, wherein the adhesive composition has a peel force from 1 to 20 N.

35. The urine collector according to claim 29, wherein the hydrophilic silicone elastomer is a polyorganosiloxane elastomer.

36. The urine collector according to claim 29, wherein the hydrophobic silicone elastomer is a polyorganosiloxane elastomer.

37. The urine collector according to claim 29, wherein the hydrophilic silicone elastomer and the hydrophobic silicone elastomer are based on the same silicone elastomer.

* * * * *

UNITED STATES PATENT AND TRADEMARK OFFICE
CERTIFICATE OF CORRECTION

| | | |
|---|---|---|
| PATENT NO. | : 8,124,675 B2 | Page 1 of 1 |
| APPLICATION NO. | : 12/923943 | |
| DATED | : February 28, 2012 | |
| INVENTOR(S) | : Chaabana Bougherara | |

It is certified that error appears in the above-identified patent and that said Letters Patent is hereby corrected as shown below:

On the Title Page,

There is a typographical error in the application number of the first claimed Foreign Priority application.

Item (30) "Foreigh Applicaton Priority Data" should be corrected to reflect:

Item (30)     Foreign Application Priority Data

Sept. 2, 2003      (DK)........................ 2003 01256
Dec. 17, 2003      (DK)........................ 2003 01871

Signed and Sealed this
Fifteenth Day of October, 2013

Teresa Stanek Rea
*Deputy Director of the United States Patent and Trademark Office*